US009022032B2

(12) United States Patent
Holzrichter

(10) Patent No.: US 9,022,032 B2
(45) Date of Patent: May 5, 2015

(54) SYSTEM FOR CONTROLLING APNEA

(75) Inventor: John F. Holzrichter, Berkeley, CA (US)

(73) Assignee: Lawwrence Livermore National Security, LLC, Livermore, CA (US)

( * ) Notice: Subject to any disclaimer, the term of this patent is extended or adjusted under 35 U.S.C. 154(b) by 494 days.

(21) Appl. No.: 13/425,133

(22) Filed: Mar. 20, 2012

(65) Prior Publication Data
US 2012/0240934 A1    Sep. 27, 2012

Related U.S. Application Data

(60) Provisional application No. 61/454,798, filed on Mar. 21, 2011.

(51) Int. Cl.
*A61M 11/00* (2006.01)
*A61N 1/36* (2006.01)
*A61B 5/08* (2006.01)

(52) U.S. Cl.
CPC ............ *A61N 1/3601* (2013.01); *A61B 5/0826* (2013.01)

(58) Field of Classification Search
CPC ............ A61M 16/06; A61M 2230/60; A61M 2205/8206; A61M 2205/3375
USPC .......... 128/204.18, 204.21, 204.23; 600/529, 600/546
See application file for complete search history.

(56) References Cited

U.S. PATENT DOCUMENTS

| | | | |
|---|---|---|---|
| 5,107,855 A | 4/1992 | Harrington et al. | |
| 5,458,137 A | 10/1995 | Axe et al. | |
| 5,617,846 A | 4/1997 | Graetz et al. | |
| 5,729,694 A | 3/1998 | Holzrichter et al. | |
| 5,953,713 A * | 9/1999 | Behbehani et al. | 706/16 |
| 6,006,175 A | 12/1999 | Holzrichter | |
| 6,411,843 B1 * | 6/2002 | Zarychta | 600/546 |
| 7,644,714 B2 | 1/2010 | Atkinson et al. | |
| 7,789,837 B2 * | 9/2010 | Lehrman et al. | 600/538 |
| 8,375,944 B2 * | 2/2013 | Kwok | 128/204.18 |
| 2006/0174883 A1* | 8/2006 | Aylsworth et al. | 128/204.21 |
| 2007/0277818 A1 | 12/2007 | Chen | |
| 2008/0109047 A1 | 5/2008 | Pless | |

* cited by examiner

*Primary Examiner* — Steven Douglas
(74) *Attorney, Agent, or Firm* — Eddie E. Scott

(57) ABSTRACT

An implanted stimulation device or air control device are activated by an external radar-like sensor for controlling apnea. The radar-like sensor senses the closure of the air flow cavity, and associated control circuitry signals (1) a stimulator to cause muscles to open the air passage way that is closing or closed or (2) an air control device to open the air passage way that is closing or closed.

9 Claims, 3 Drawing Sheets

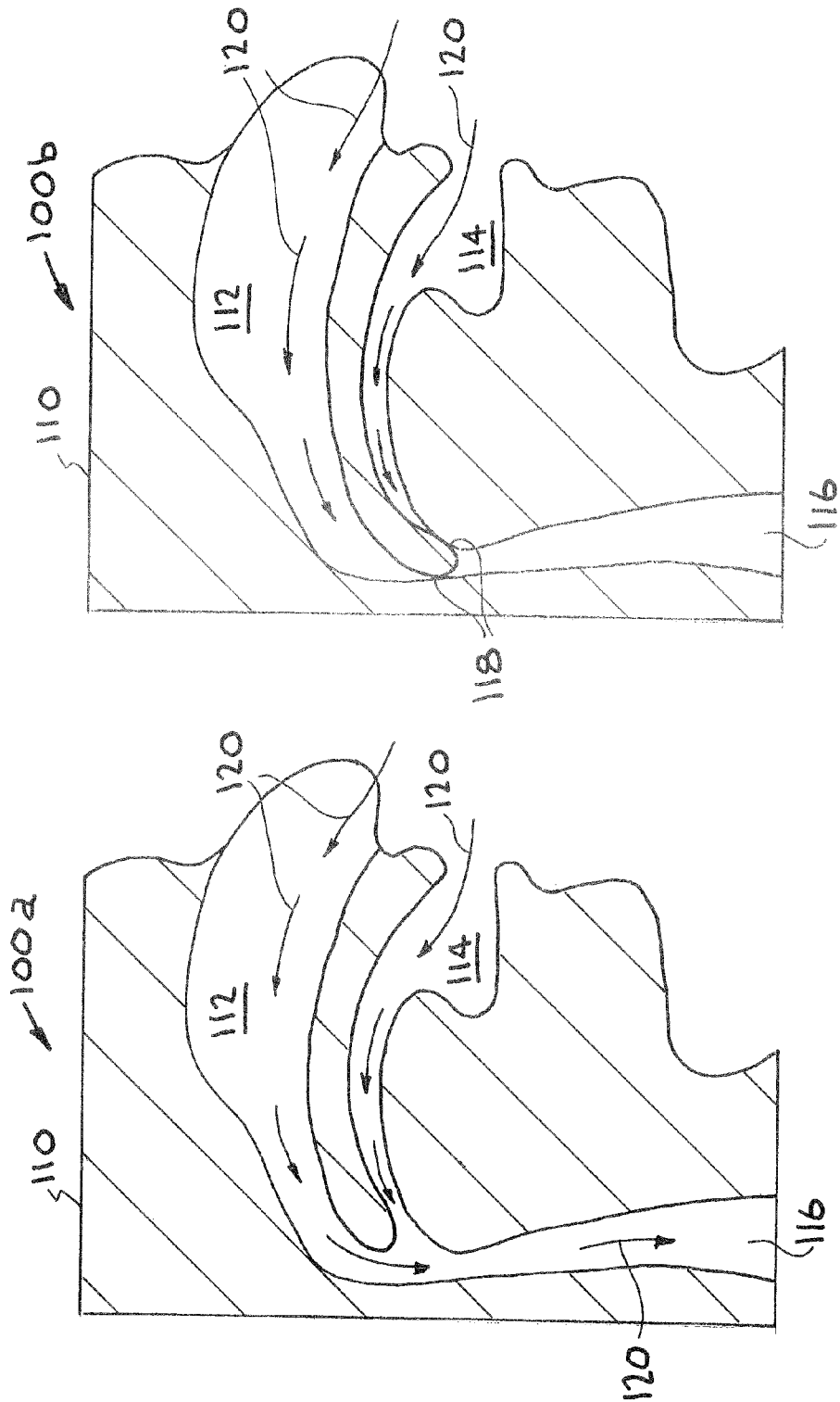

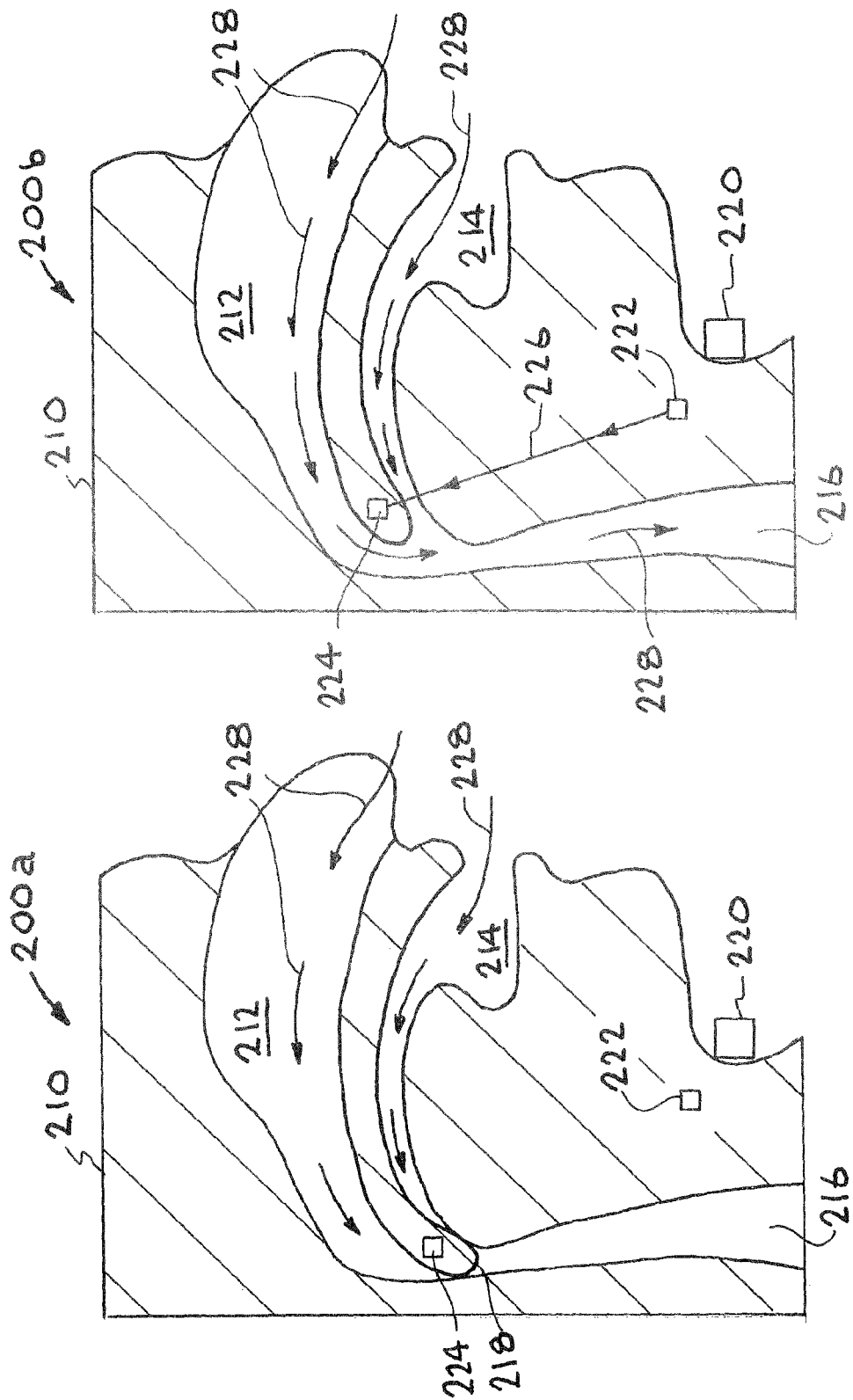

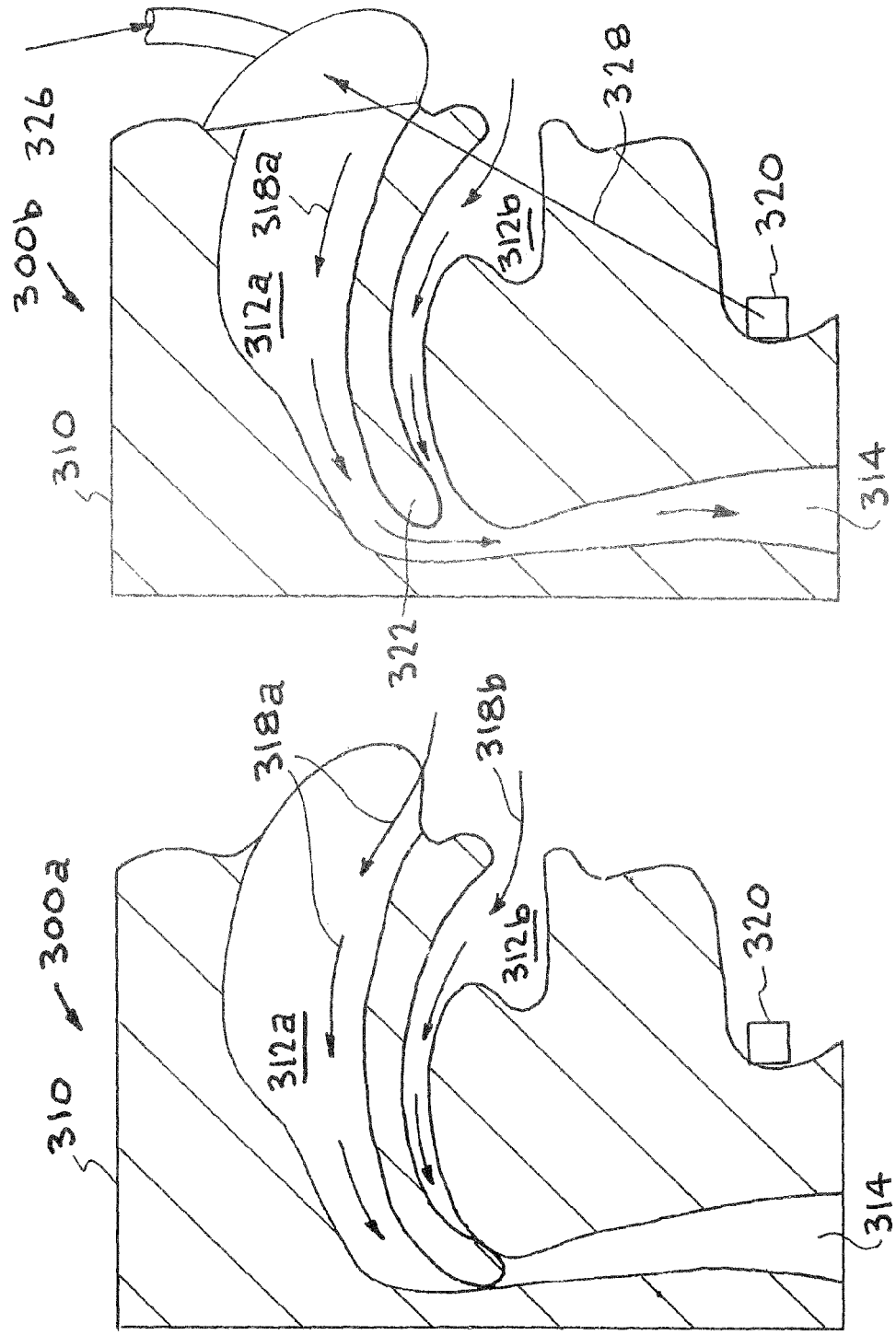

SYSTEM FOR CONTROLLING APNEA

CROSS-REFERENCE TO RELATED APPLICATIONS

This application claims benefit under 35 U.S.C. §119(e) of U.S. Provisional Patent Application No. 61/454,798 filed Mar. 21, 2011 entitled "Method, Apparatus, and System for Controlling Apnea," the disclosure of which is hereby incorporated by reference in its entirety for all purposes.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present invention relates to apnea and more particularly to a system for controlling apnea.

2. State of Technology

U.S. Pat. No. 5,5107,855 to Reginald Harrington and Raph Crossley for an Apnea monitor for detection of a periodic sinusoidal movement issued Apr. 28, 1992 provides the following state of technology information:

"Various previous sleep apnea alarm devices have been proposed for monitoring the breathing particularly of infants during sleep but also the breathing of adults who may have breathing difficulties."

"There are a number of areas of difficulty in such devices and these difficulties have to date substantially prevented any effective device from being available in the marketplace."

"Firstly there is the difficulty of initially detecting the movement of the muscles. Many arrangements have used devices which detect pressure changes caused by movement of the patient on a mattress but these devices have proven to be unreliable. Alternative techniques use a band or similar equipment attached around the patient particularly in the thoracic area. The extension and contraction of the band is then detected in some cases by strain gauges and in other cases by movement of one element which varies a capacitive coupling. Again these devices have proven to be unreliable."

"A second area of difficulty relates to the communication of the information from the detecting device to a receiving device mounted separately from the patient. In most cases a wire coupling is used but this is of course highly unsatisfactory and it can restrict movement of the patient and can be dangerous should the patient become entangled in the wire coupling."

"A third area of difficulty relates to the analysis of the information from the detection device mounted on the patient. In most cases the analysis is very simplistic and can fail to distinguish between the required breathing patterns and any other type of movement."

"Basically therefore it is absolutely essential in a device of this type to provide a device which is reliable in that it acts to trigger an alarm whenever breathing difficulties are encountered but at the same time the device must be able to properly distinguish from other conditions caused for example by movement of the patient away from a preferred detecting location which would cause the alarm to be actuated when no emergency condition is present. Such an alarm device which produces a number of false alarms will of course rapidly lose any credibility and will no longer be used."

U.S. Pat. No. 5,617,846 to Bernd Graetz and Jorg Maurer for a method of controlling a respirator for treatment of sleep apnea and device for carrying out the method issued Apr. 8, 1997 provides the following state of technology information:

"A not insignificant number of people suffer from sleep disorders which have an impact on those people's well-being during the day and which partly have a significant effect on their social and professional efficiency as well as on their quality of life. One of these sleep disorders is sleep apnea, which is primarily treated with the so-called CPAP-therapy (CPAP=Continuous Positive Airway Pressure) by continuously supplying an air stream of a respiration gas to the patient during his sleep via a nasal mask. Via a tube, the mask is connected with a device for respiration comprising a ventilator that generates a gas stream with an overpressure of 5 to 20 mbar,"

"The gas stream is supplied to the patient either at a constant pressure or it is lowered to a lower pressure level in order to ease the breathing effort of the patient during exhaling. Although sleep apneas occur only briefly and are only a very small portion of the sleeping period, the ventilator in both methods runs during the entire sleeping period (night) and thus renders the acceptance of this sleep apnea treatment difficult."

U.S. Pat. No. 7,644,714 to Robert E. Atkinson and Chad J. Kugler for a method of controlling devices and methods for treating sleep disorders issued Jan. 12, 2010 provides the following state of technology information:

"Obstructive sleep apnea (OSA) is a highly prevalent sleep disorder affecting an estimated 18 million people in the United States, and an estimated 36 million people world wide. Furthermore, the affected population is estimated to be growing at 22% per annum. OSA is not just a quality of sleep issue. OSA has several co-morbidities that drive treatment, including heart failure, hypertension, myocardial infarction, stroke, and diabetes. Despite the seriousness of the condition, it is estimated that only 5% to 8% of the affected population have been diagnosed and treated."

"Approximately 80% of the patients diagnosed with OSA are prescribed continuous positive airway pressure (CPAP) therapy. Although CPAP is the first line of treatment for the majority of patients and is considered the gold-standard by most practitioners, it enjoys only 30-60% average patient compliance. Approximately 10-15% of patients will have surgical treatment, but the surgical options tend to be invasive and are not always effective. Approximately 5-10% of patients will use a mandibular advancement device, but such devices tend to have limited efficacy and are often associated with joint pain."

"Thus, there is a need for improved OSA treatment devices in terms of patient compliance, invasiveness and efficacy."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a stimulator or air control system that is activated by a radar-like sensor for controlling apnea. The radar sensor senses the closure of the air flow cavity, and associated control circuitry signals the stimulator to cause muscles to open the air passage way that is closing or closed or signals the air control system that is used to activate the air control system.

The present invention has use for enabling persons having apnea problems to correct their problem in a way that is automatic and non-intrusive. The present invention is especially useful for controlling sleep apnea which disturbs the sleep of millions of persons worldwide. In addition, the present invention can be used to control snoring which is caused by air passage tissue partial or temporary closure generating objectionable breathing noise, during sleep.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

FIG. 1A is an illustration showing an individual with unobstructed air passages.

FIG. 1b is an illustration showing an individual with obstructed air passages.

FIG. 2A is an illustration showing an individual with obstructed air passages, an implanted stimulation device, and an external radar-like sensor.

FIG. 2B is an illustration showing an individual with obstructed air passages, an implanted stimulation device, an external radar-like sensor, and a signal from the external radar-like sensor to the implanted stimulation device.

FIG. 3A is an illustration showing an individual with obstructed air passages and an external radar-like sensor.

FIG. 3B is an illustration showing an individual with obstructed air passages, an air control system, an external radar-like sensor, and a signal from the external radar-like sensor to the air control system.

DETAILED DESCRIPTION OF SPECIFIC EMBODIMENTS

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to the drawings and in particular to FIG. 1A, an individual with unobstructed air passages is illustrated. The individual having unobstructed air passages is designated generally by the reference numeral 100a. The illustration in FIG. 1A shows the head 110 of the individual 100a. The head 110 has nasal cavities 112, mouth 114, and trachea 116. The arrows 120 show the flow of air and that the individual 100a has unobstructed air passages. The air 120 flows freely through the mouth 114, the nasal cavities 112, and the trachea 116.

Referring now to FIG. 1B, an individual with obstructed air passages is illustrated. The individual having obstructed air passages is designated generally by the reference numeral 100b. FIG. 1B is an illustration of sleep apnea, a common disorder in which one or more pauses in breathing or shallow breaths while an individual is sleeping. Individuals with low muscle tone and soft tissue around the airway and structural features can give rise to a narrowed airway wherein the flow of air 120 is blocked by tissue 118. The FIG. 1B illustration shows the head 110 of the individual 100b. The head 110 has nasal cavities 112, mouth 114, and trachea 116. The arrows 120 show the flow of air and that the individual 100b has obstructed air passages. The air 120 enters the mouth 114 and the nasal cavities 112 but is blocked from passing through the trachea 116. As illustrated in FIG. 1B the flow of air 120 is blocked by tissue 118.

Sleep apnea, a common disorder in which one or more pauses in breathing or shallow breaths while an individual is sleeping. Sleep apnea is a potentially serious sleep disorder in which breathing repeatedly stops and starts. An individual may have sleep apnea if the individual snores loudly and feels tired even after a full night's sleep. Sleep apnea occurs in two main types (1) Obstructive sleep apnea, the more common form that occurs when throat muscles relax and (2) Central sleep apnea, which occurs an individual's your brain doesn't send proper signals to the muscles that control breathing. Some individuals have complex sleep apnea, which is a combination of both.

The present invention provides (1) a stimulator or (2) an air control system that are activated by a radar-like sensor for detecting and then controlling apnea. The radar sensor senses the closure of the air flow cavity, and associated control circuitry signals (1) the stimulator to cause muscles to open the air passage way that is closing or closed or (2) signals the air control system that is used to activate the air control system. In one embodiment, the present invention provides an implanted stimulation device that is activated by an external radar-like sensor. The radar-like sensor senses the closure of the air flow cavity and associated control circuitry signals a stimulator to cause muscles to open the air passage way that is closing. In another embodiment, the present invention provides an air control device that is activated by an external radar-like sensor. The radar-like sensor senses the closure of the air flow cavity and associated control circuitry signals the air control device.

The present invention consists of two parts (1) sensor sub-system and (2) stimulator/air control sub-system. They can each be placed in separate locations in the body or outside the body, and connected together wirelessly or with wires. One embodiment of the present invention utilizes a small radar like sensor attached to the user's neck via a necklace, tape, or other technique and a stimulator system that is placed in or near the tissues needing control. Another system utilizes a small radar-like sensor which detects apnea and then energizes a forced air device upon detection of closure.

DEFINITIONS OF TERMS

The terms tissues and muscles are used interchangeably in this application.

The terms "stimulator" and "heart pace-maker-like device" and "pacemaker cell" as used in this application mean an electronic stimulation system to cause body tissue, including smooth muscles lining the air passage ways, to respond.

Different embodiments of the present invention include various subsystems and combination of subsystems. The subsystems provide a sensor and an air passage muscle-stimulator system. For example, the subsystems may include of one or more of the following devices.

Radar or EM Sensor

A radar or similar EM sensor of the types described by Holzrichter et al for speech organ measurements and by Chang et al for hematoma detection is placed outside or inside the patients neck area to sense the closure, partial or complete, of the patient's air passages. The signal between the radar/controller and the stimulator may be carried wirelessly, if the radar is located outside of the patient's skin. A sensor and stimulator may be placed inside the muscle tissue and controlled by a radar sensor/controller or the sensor may energize a typical forced-air apnea corrector.

Heart Pace-Maker-Like Device

A heart pace-maker-like device which is inserted just under the neck skin and is then attached to a wire that is embedded in the muscle tissues that close the air passage during sleep (and/or during other occasions). The stimulator is connected to an external or internal-body located radar device that detects air passage muscle closure and which issues a control signal to the implanted device. Alternatively, it may issue a control signal to an air corrector device.

Both sub systems need electrical power to work properly. Hence they use batteries for normal use. The batteries can be attached to charging circuits that enable recharging using magnetic induction, e.g., while wearing a radar sensor on the neck at night which also has a magnetic induction generator unit within it. Or batteries can be replaced inside the body every few years (as is used in heart pacemaker technology). If the radar/controller is worn outside the body, battery replacement or battery charging is simple to accomplish on the controller, since the device would normally be worn only at night. If the stimulator part of the invention is implanted, then a means to either replace a battery via surgery, or recharging by magnetic induction, is used.

EXAMPLES

Referring now to FIGS. 2A and 2B, examples of one embodiment of a system of the present invention for controlling sleep apnea are shown. FIG. 2A is an illustration showing an individual with obstructed air passages, an implanted stimulation device, and an external radar-like sensor. FIG. 2B is an illustration showing an individual with obstructed air passages, an implanted stimulation device, an external radar-like sensor, and a signal from the external radar-like sensor to the implanted stimulation device.

Referring now to FIG. 2A an individual with obstructed air passages is shown. The individual having obstructed air passages is designated generally by the reference numeral 200a. The FIG. 2A illustration shows the head 210 of the individual 200a. The head 210 has nasal cavities 212, mouth 214, and trachea 216. The arrows 228 show the flow of air and that the individual 200a has obstructed air passages. The air 228 enters the mouth 214 and the nasal cavities 212 but is blocked from passing through the trachea 216. As illustrated in FIG. 2A the flow of air 228 is blocked by tissue 218.

The present invention provides a radar-like sensor 220 that senses the closure of the air flow cavity and a stimulator 224 that causes the muscles to open the air passage way that is closing or closed. The radar-like sensor 220 is a radar or similar EM sensor of the type described by Holzrichter et al for speech organ measurements including the descriptions in U.S. Pat. Nos. 5,729,694 and 6,006,175. The disclosures of U.S. Pat. Nos. 5,729,694 and 6,006,175 are incorporated herein by this reference. The stimulator 224 is a "heart pace-maker-like device" or "pacemaker cell" and these terms as used in this application mean an electronic stimulation system.

The radar-like sensor 220 is normally placed outside or inside the neck area of the individual 200a to sense the closure, partial or complete, of the individual's air passages 212, 214, and 216. However, it may be placed inside also. The stimulator 224 is a heart pace-maker-like device which is attached to a wire that is embedded in the muscle tissues that close the air passage during sleep (and/or during other occasions). The stimulator 224 is connected to the sensor 220 that detects air passage muscle closure and issues a control signal to the implanted stimulator 224.

Referring now to FIG. 2B, an illustration shows an individual with obstructed air passages being opened, an implanted stimulation device, an external radar-like sensor, and a signal from the external radar-like sensor to the implanted stimulation device. The individual having obstructed air passages opened is designated generally by the reference numeral 200a. The FIG. 2B illustration shows the head 210 of the individual 200a. The head 210 has nasal cavities 212, mouth 214, and trachea 216. The arrows 228 show the flow of air through the air passages of the individual 200a. The air 228 enters the mouth 214 and the nasal cavities 212 and flows to the trachea 216 because the previously obstructed air passages have been opened.

The radar-like sensor 220 had sensed the closure of the air flow cavity and a stimulator 224 had caused the muscles to open the air passage way that was closing or closed. The signal 226 between the sensor 220 and the stimulator 224 is carried wirelessly or via a conductor.

Referring now to FIGS. 3A and 3B, an additional example of an embodiment of the present invention for controlling sleep apnea is shown. FIG. 3A is an illustration showing an individual with obstructed air passages and an external radar-like sensor system of the present invention in position, FIG. 3B is an illustration showing an individual with obstructed air passages, an external radar-like sensor system of the present invention in position, an air control device, and a signal from the external radar-like sensor system to the air control device.

Referring to FIG. 3A an individual with obstructed air passages is shown. The individual having obstructed air passages is designated generally by the reference numeral 300a. The FIG. 3A illustration shows the head 310 of the individual 300a. The head 310 has cavities 312a (nasal) and 312b (oral cavity and throat), and trachea 314. The arrows 318a and 318b illustrate the flow of air in cavities 312a (nasal) and 312b (oral to throat). As illustrated in FIG. 3A, the individual 300a has obstructed air passages at 322. The air represented by arrows 318a and 318b enters the cavities 312a (nasal) and 312b (oral throat) but is blocked from passing through the trachea 314 by tissue 322.

The present invention provides a radar-like sensor 320 that senses the air passages that are closing or are closed. The radar-like sensor 320 is a radar or similar EM sensor of the type described by Holzrichter et al for speech organ measurements including the descriptions in U.S. Pat. Nos. 5,729,694 and 6,006,175. The disclosures of U.S. Pat. Nos. 5,729,694 and 6,006,175 are incorporated herein by this reference. The radar-like sensor 320 is placed outside or inside the neck area of the individual 300*a* to sense the closure, partial or complete, of the individual's air passages 312*a*, 312*b*, and 314.

Referring now to FIG. 3B, an illustration shows the individual with obstructed air passage 322, an external radar-like sensor system of the present invention in position, an air control device, and a signal from the external radar-like sensor system to the air control device. The individual is designated generally by the reference numeral 300*b*. The FIG. 3B illustration shows the head 310 of the individual 300*b*. The head 310 has cavities 312*a* (nasal) and 312*b* (throat), and trachea 314. The arrow 318*a* illustrates the flow of air in the cavity 312*a* (nasal). The air 318*a* enters the nasal cavity 312*a* and flows to the trachea 314 because the previously obstructed air passages have been opened by the air control device 324.

The air control device 324 is in the form of a mask positioned over the nasal cavity 321*a*. The radar-like sensor 320 has sensed the closure of the air flow cavity and a signal 328 has been carried by wire or wirelessly to the air control device 324. The air control device 324 has an air inlet illustrated by the arrow 326. When the air control device 324 receives the signal it turns on and forces air 326 into the nasal cavity 312*a* to open the passage to the trachea 314. The soft tissue 322 has moved to allow the passage of air to the trachea 314. The air control device 324 can be any of the air control systems disclosed in U.S. Published Patent Application No. 2007/0277818 by Chung-Chu Chen for a "method and apparatus for treating obstructive sleep apnea by using negative oral pressure to a patient" published Dec. 6, 2007. The disclosure of U.S. Published Patent Application No. 2007/0277818 by Chung-Chu Chen for a "method and apparatus for treating obstructive sleep apnea by using negative oral pressure to a patient" is incorporated herein by this reference. Other systems using full face masks, breathing tubes, and other techniques for forcing air to enter the lungs or be removed from the lungs are also part of the present invention.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus for controlling an individual's air passages being potentially blocked by the individual's soft tissue around the air passages wherein the individuals air passages are in the individuals neck area, comprising:
   an EM wave generator and receiver operatively positioned in the individuals neck area for directing EM waves to the individual's soft tissue and receiving EM waves from the individuals soft tissue,
   an air system operatively connected to the individual's air passages for forcing air into the individuals air passages, and
   a controller operatively connected to said EM wave generator and receiver and operatively connected to said air system to signal said air system when the individual's air passages are potentially being blocked by the individual's soft tissue to force air into the individuals air passages to move the individuals soft tissue and un-block the individuals air passages.

2. The apparatus for controlling an individual's air passages being potentially blocked by the individual's soft tissue of claim 1 wherein the individual has lungs that have air wherein said air system operatively connected to the air passages includes an air mask for forcing air into the individuals air passages.

3. The apparatus for controlling an individual's air passages being potentially blocked by the individual's soft tissue of claim 1 wherein said EM wave generator and receiver includes an antenna which radiates EM waves to the individual's soft tissue and receives EM waves from the individual's soft tissue.

4. The apparatus for controlling an individual's air passages being potentially blocked by the individual's soft tissue of claim 1 wherein the individual has an air tract tissue-target and wherein said EM wave generator and receiver includes an antenna which radiates EM waves to said air tract tissue-target and receives EM waves from the individual's air tract tissue-target.

5. The apparatus for controlling an individual's air passages being potentially blocked by the individual's soft tissue of claim 4 wherein said antenna has a far-field and wherein said antenna directs said EM waves to the individual's soft tissue and receives EM waves from the individual's soft tissue.

6. The apparatus for controlling an individual's air passages being potentially blocked by the individual's soft tissue of claim 1 further comprising recharging units for said EM wave generator and receiver.

7. The apparatus for controlling an individual's air passages being potentially blocked by the individual's tissue of claim 1 further comprising one or more recharging units for said controller.

8. An apparatus for controlling an individual's air passages being potentially blocked by the individual's soft tissue around the passages wherein the individuals air passages are in the individuals neck area, comprising:
   EM wave generator and receiver means positioned in the individuals neck area of the individual's soft tissue and receiving EM waves from the individuals soft tissue,
   controller means operatively connected to said EM wave generator and receiver for signaling when the individual's air passages are potentially being blocked by the individual's soft tissue, and
   air system means operatively connected to the individual's air passages for forcing air into the individuals air passages upon said signaling to move the individuals soft tissue and un-block the individuals air passages.

9. The apparatus for controlling an individual's air passages being potentially blocked by the individual's soft tissue of claim 8 wherein the individual has lungs and wherein said air system means operatively connected to the individual's air passages for forcing air into the individuals air passages upon said signaling to move the individuals soft tissue and un-block the individuals air passages comprises an air mask which forces said air into the individual's lungs upon said signaling.

\* \* \* \* \*